(12) United States Patent
De Angeli et al.

(10) Patent No.: US 12,708,714 B2
(45) Date of Patent: Aug. 18, 2026

(54) FORCE SENSOR FOR MEDICAL DEVICES

(71) Applicant: Flextronics AP, LLC, San Jose, CA (US)

(72) Inventors: Marco De Angeli, Barzana (IT); Antonino Bongiovanni, Milan (IT)

(73) Assignee: Flextronics AP, LLC, San Jose, CA (US)

(*) Notice: Subject to any disclaimer, the term of this patent is extended or adjusted under 35 U.S.C. 154(b) by 405 days.

(21) Appl. No.: 18/396,911

(22) Filed: Dec. 27, 2023

(65) Prior Publication Data

US 2024/0350741 A1 Oct. 24, 2024

Related U.S. Application Data

(60) Provisional application No. 63/470,684, filed on Jun. 2, 2023, provisional application No. 63/461,072, filed on Apr. 21, 2023.

(51) Int. Cl.

*A61M 5/315* (2006.01)
*G01L 1/14* (2006.01)
*G01L 5/22* (2006.01)

(52) U.S. Cl.

CPC ......... *A61M 5/31568* (2013.01); *G01L 1/142* (2013.01); *G01L 5/22* (2013.01); *A61M 2205/332* (2013.01); *A61M 2205/50* (2013.01); *A61M 2205/8206* (2013.01)

(58) Field of Classification Search

CPC ........ A61M 5/31568; A61M 2205/332; A61M 2205/50; A61M 2205/8206; G01L 1/142; G01L 5/22

See application file for complete search history.

(56) References Cited

U.S. PATENT DOCUMENTS

| | | | |
|---|---|---|---|
| 2019/0321555 A1 | 10/2019 | Biondi et al. | |
| 2020/0078527 A1* | 3/2020 | Biederman | A61M 5/31586 |
| 2020/0206424 A1 | 7/2020 | Rios et al. | |
| 2021/0128841 A1* | 5/2021 | Andersen | A61M 5/31515 |
| 2021/0330891 A1* | 10/2021 | Byerly | A61M 5/20 |

FOREIGN PATENT DOCUMENTS

WO 2016162298 A1 10/2016

* cited by examiner

*Primary Examiner* — Tasnim Mehjabin Ahmed
(74) *Attorney, Agent, or Firm* — Volpe Koenig

(57) ABSTRACT

A syringe includes a barrel and a plunge rod axially translatable within the barrel. The plunge rod includes a plunge end extending outside the barrel. A smart cap is coupled to the plunge end of the plunge rod. The smart cap includes a spring, a conductive plate coupled to the spring, a spacer, a battery holder, a battery, a measuring device, and a cap. The battery holder is disposed axially closer to the plunge end than the spacer, and the battery holder is adjacent a first surface of the battery. The measuring device is disposed axially closer to the plunge end than the battery holder, and the measuring device is adjacent a second surface of the battery. The cap is axially aligned with the plunge rod. The cap encompasses each of the spring, the conductive plate, the spacer, the battery holder, the battery, and the measuring device.

16 Claims, 3 Drawing Sheets

FORCE SENSOR FOR MEDICAL DEVICES

CROSS REFERENCE TO RELATED APPLICATIONS

This application claims the benefit of U.S. Provisional Application No. 63/470,684 filed on Jun. 2, 2023 and U.S. Provisional Application No. 63/461,072 filed on Apr. 21, 2023, which is incorporated by reference as if fully set forth.

FIELD OF THE INVENTION

The present disclosure is directed to disposable syringes, and more particularly it is directed to a disposable syringe including a smart cap with force sensing capabilities.

BACKGROUND OF THE INVENTION

As is readily known, a syringe is a pumping device generally including a plunger disposed tightly within a cylindrical tube or barrel, and syringes are generally used in the medical industry to inject and dispense a fluid, such as liquid medication. Recently, there is a desire to obtain more data related to medical procedures to improve clinical trials and the overall health of patients. Therefore, smart syringes have been developed which are utilized to collect injection information, provide more refined insights, and perform better statistical analysis of medical trial outcomes. For example, traditional smart syringes can be configured to record one or more of the following: time of injection, duration of injection, dose administered, drug name, expiry date, and other similar data. An issue arises when introducing the smart syringe technology into disposable syringes due to the higher costs associated with smart syringes and the disposable nature of disposable syringes, resulting in an expensive disposable product.

Therefore, there is a need for a cost effective disposable syringe that utilizes traditional smart syringe technology, as well as includes further capabilities to collect data that has not previously been collected using smart syringe technology.

SUMMARY OF THE INVENTION

According to one aspect, the present disclosure is directed to a syringe including a smart cap. The syringe can include a barrel and a plunge rod axially translatable within the barrel along an axis of the plunge rod. The plunge rod can include a plunge end extending outside the barrel. The smart cap can be coupled to the plunge end of the plunge rod extending outside the barrel. The smart cap can include a spring, a conductive plate, a spacer, a battery holder, a battery, a measuring device, and a cap. The spring can include the conductive plate coupled to the spring. The spacer can be disposed axially closer to the plunge end than the spring and the conductive plate. The battery holder can be disposed axially closer to the plunge end than the spacer. The battery holder can be positioned adjacent a first surface of the battery. The measuring device can be disposed axially closer to the plunge end than the battery holder. The measuring device can be positioned adjacent a second surface of the battery. The cap can be axially aligned with the plunge rod. The cap can encompass each of the spring, the conductive plate, the spacer, the battery holder, the battery, and the measuring device.

In one aspect, a spring extension of the spring is coupled to a surface of the measuring device facing the plunge end.

In one aspect, the conductive plate is coupled to a surface of the spring facing the battery holder.

In one aspect, the conductive plate is axially offset from the battery holder, with the spacer being positioned between an axial underside of the conductive plate and an axial topside of the battery holder.

In one aspect, an axial underside of the battery holder abuts an axial topside of the battery, and an axial topside of the measuring device abuts an axial underside of the battery.

In one aspect, a battery holder extension of the battery holder is coupled to a surface of the measuring device facing the plunge end.

In one aspect, the measuring device is a printed circuit board.

In one aspect, the printed circuit board is configured to record capacitance measurements and store the capacitance measurements within a memory of the printed circuit board.

In one aspect, the smart cap is configured as a variable capacitor force sensor.

In one aspect, the variable capacitor force sensor is constructed from a first electrode and a second electrode, the first electrode being the conductive plate coupled to the spring and the second electrode being one of the battery or the battery holder.

In one aspect, a force applied to the smart cap causes the plunge rod to translate axially into the barrel, the force causes the first electrode to axially translate towards the second electrode within the cap, and a change in capacitance measured by the measuring device indicates a value of the force applied to the smart cap.

In one aspect, the variable capacitor force sensor is constructed from a first electrode and a second electrode, the first electrode being the conductive plate coupled to the spring and the second electrode being a conductive copper pad of the measuring device.

In one aspect, the measuring device, the battery, the battery holder, the spacer, the conductive plate, and the spring are positioned axially in order from the plunge end of the plunge rod in an axial direction extending away from the plunge end and the barrel.

In one aspect, the syringe is a pre-filled disposable syringe.

In one aspect, a light source of the smart cap is configured to illuminate once a compression force applied to the smart cap exceeds a predefined limit.

In one aspect, each of the spring, the conductive plate, the spacer, the battery holder, the battery, and the measuring device are axially aligned with the axis of the plunge rod.

According to one aspect, the present disclosure is directed to a variable capacitor force sensor. The variable capacitor force sensor can include a first electrode, a second electrode, and a measuring device. The first electrode can be a conductive plate coupled to a spring. The second electrode can be a battery holder, a battery, or a copper pad. The measuring device can be configured to record capacitance measurements between the first electrode and the second electrode, and the change in capacitance measured by the measuring device indicates a value of the force applied to the variable capacitor force sensor.

In one aspect, the measurement device is a printed circuit board.

In one aspect, the copper pad is coupled to the measuring device.

In one aspect, the variable capacitor force sensor is disposed within a smart cap, and the smart cap is coupled to a plunge end of a plunge rod of a syringe.

BRIEF DESCRIPTION OF THE DRAWINGS

The foregoing Summary as well as the following Detailed Description will be best understood when read in conjunction with the appended drawings, which illustrate a preferred embodiment of the disclosure. In the drawings.

DETAILED DESCRIPTION OF THE PREFERRED EMBODIMENTS

Figure 1:
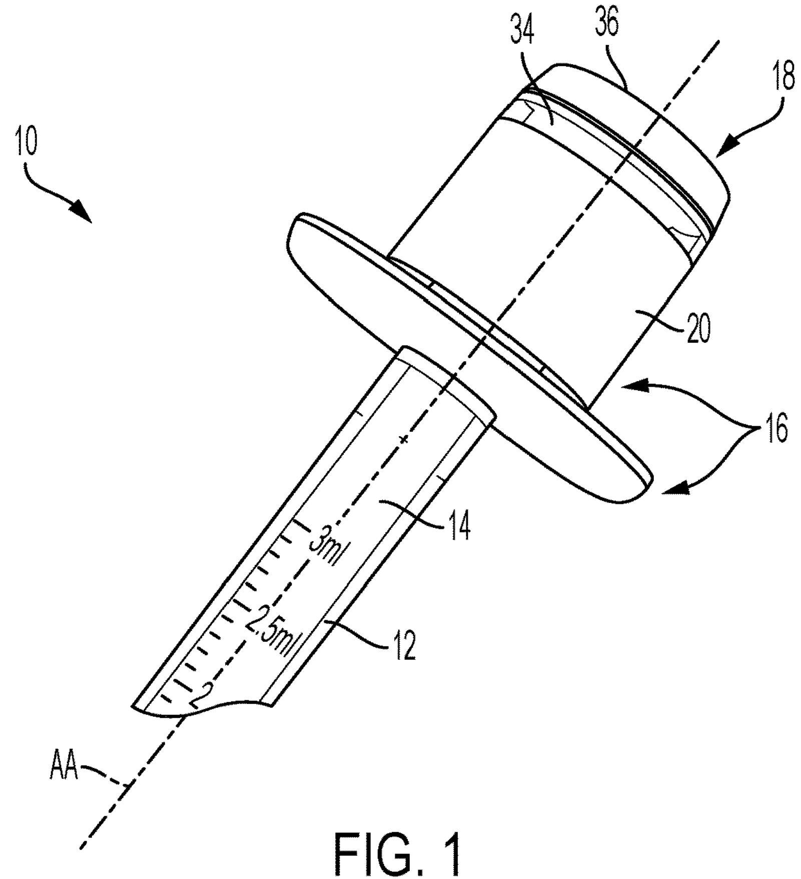
FIG. 1 is a perspective view of an end portion of a syringe according to the present disclosure.

Certain terminology is used in the following description for convenience only and is not limiting. The words "front", "rear", "upper", and "lower" designate directions in the drawings to which reference is made. The words "inwardly" and "outwardly" refer to directions towards and away from parts referenced in the drawings. "Axially" refers to a direction along the axis of a shaft, pin, tube, barrel, rod, or the like. A reference to a list of items that are cited as "at least one of a, b, or c" (where a, b, and c represent the items being listed) means any single one of the items a, b, or c, or combinations thereof are included. The terminology includes the words specifically noted above, derivatives thereof, and words of similar import.

FIG. 1 is a perspective view of an end portion of a syringe 10 according to the present disclosure. The syringe 10 is a pumping device which is generally used in the medical industry to inject and dispense a fluid such as liquid medication, among other options not specifically listed. In some examples, the syringe 10 can be a pre-filled disposable syringe, such that a user receives the syringe pre-filled with a fluid, injects the fluid, and then disposes of (throws away) the pre-filled disposable syringe. In other examples, the syringe 10 may not be a pre-filled or disposable syringe.

The syringe 10 can include a barrel 12, a plunge rod 14, a smart cap 18, and a needle (not shown). The barrel 12 is the body of the syringe 10 that houses the plunge rod 14 and the fluid to be dispensed by the syringe 10. In some examples, as illustrated, the barrel 12 can have a generally elongated cylindrical shape. In other examples, the barrel 12 can have a shape other than an elongated cylindrical shape. Disposed at the end of the barrel 12 not illustrated in FIG. 1, the needle can be coupled to the barrel 12. As is known, the needle is configured to be inserted into the user when dispensing the fluid or medication from within the syringe 10.

The plunge rod 14 is disposed tightly within the barrel 12. Specifically, the plunge rod 14 is axially aligned with the barrel 12, and the plunge rod 14 is axially translatable within the barrel 12 along an axis AA of the plunge rod 14. When pressed and/or squeezed, an end of the plunge rod 14 (not illustrated in FIG. 1) is configured to force the fluid within the barrel 12 out through the needle (not shown). The plunge rod 14 includes a plunge end 16 extending outside the barrel 12 (shown best in FIG. 2). The smart cap 18 is coupled to the plunge end 16 of the plunge rod 14 extending outside the barrel 12. The smart cap 18 is coupled to the plunge end 16 such that the smart cap 18 translates axially along the axis AA with the plunge rod 14. Further, the smart cap 18 is coupled to the plunge end 16 in such a way that when an axial force is applied to the smart cap 18, the smart cap 18 can translate (slightly) axially relative to the plunge end 16, discussed further below. In the illustrated example, the smart cap 18 includes a generally cylindrical shape. In other non-illustrated examples, the smart cap 18 can include any other geometrical shape.

Figure 2:
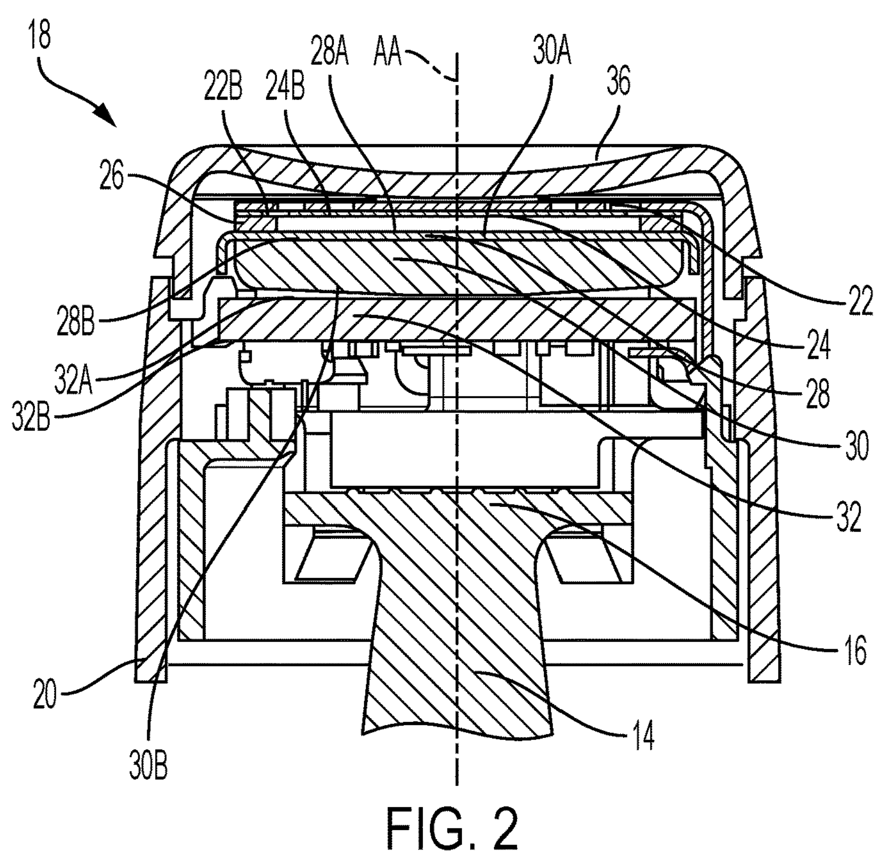
FIG. 2 is a cross-sectional view of a smart cap of the syringe of FIG. 1.
Figure 3:
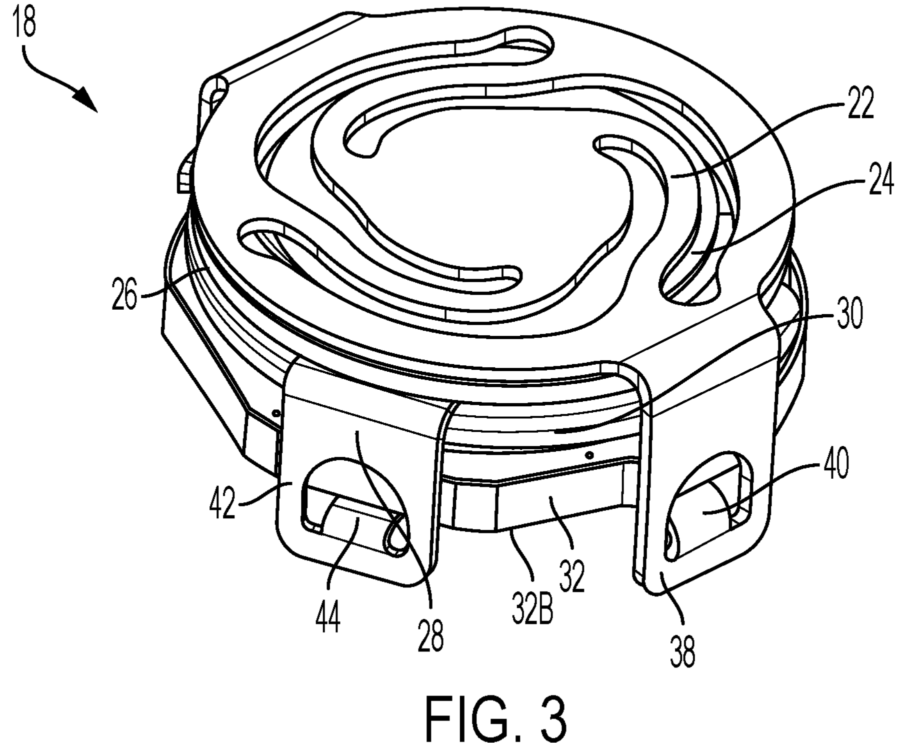
FIG. 3 is a perspective view of the smart cap with a cap removed, illustrating the components contained within the cap of the smart cap.
Figure 4:
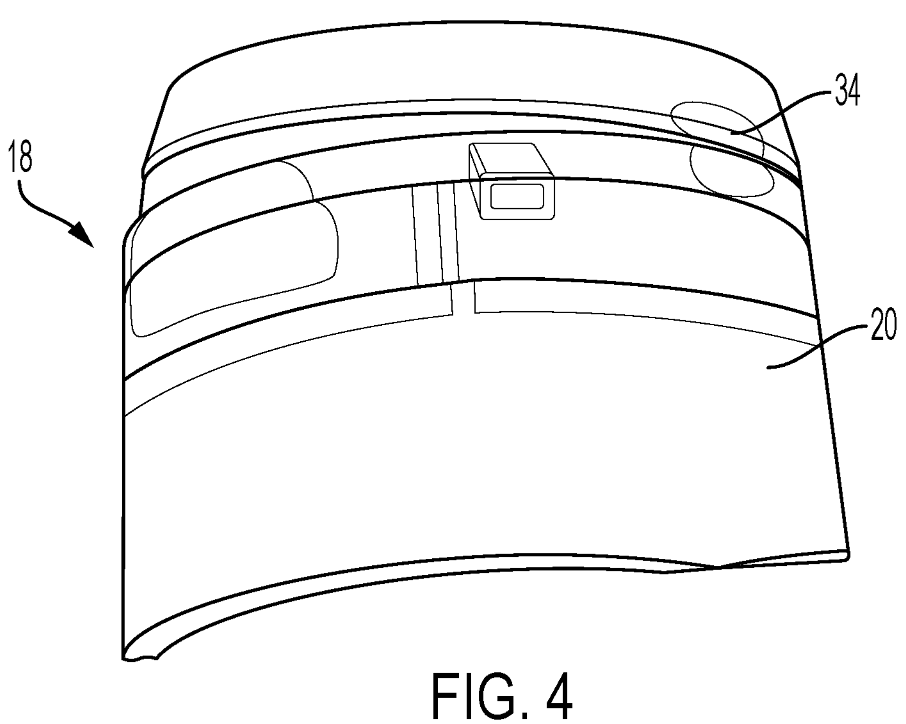
FIG. 4 is a perspective view of a glowing light source of the smart cap of FIG. 2.
Figure 5:
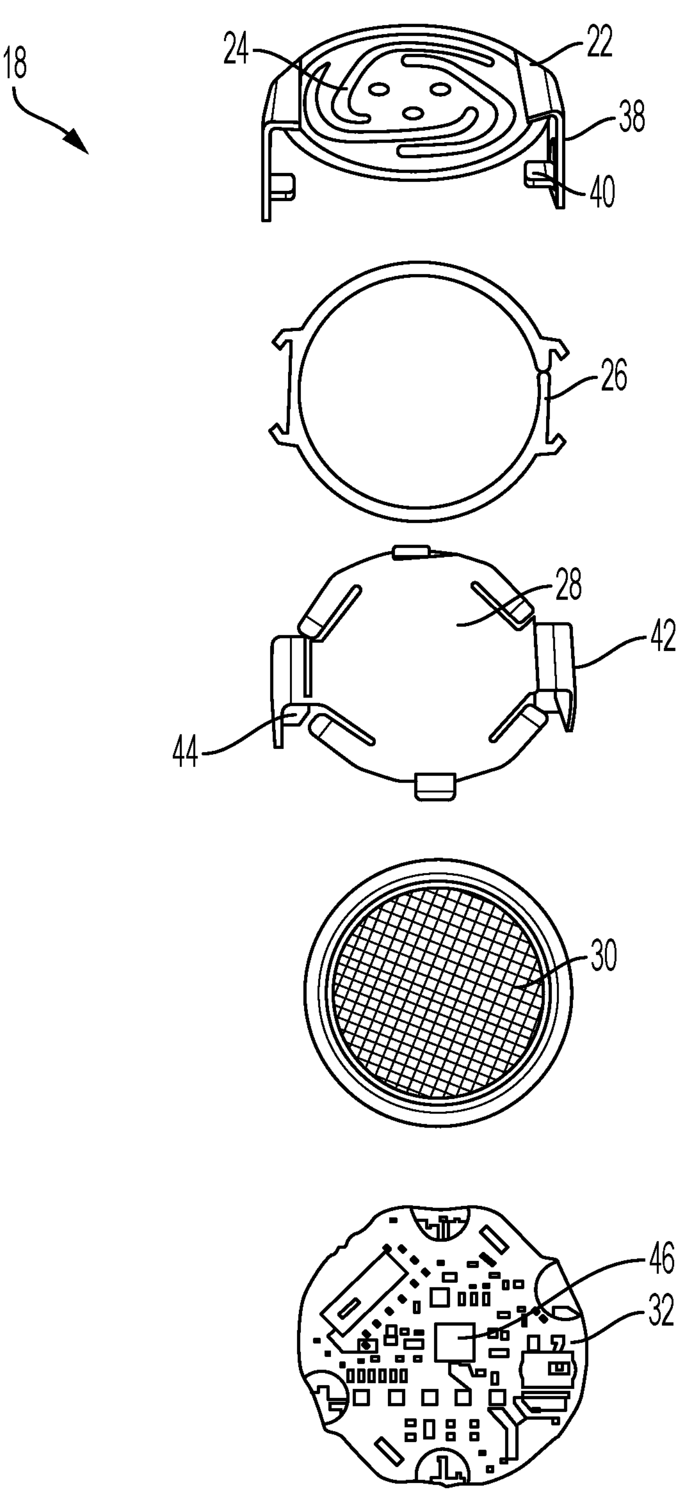
FIG. 5 is an exploded view of the smart cap, illustrating the individual components of the smart cap.

FIG. 2 is a cross-sectional view of the smart cap 18 of the syringe 10. FIG. 3 is a perspective view of the smart cap 18 with a cap 20 of the smart cap 18 removed, illustrating the components contained within the cap 20 of the smart cap 18. FIG. 4 is a perspective view of a glowing light source 34 of the smart cap 18. FIG. 5 is an exploded view of the smart cap 18, illustrating the individual components of the smart cap 18. FIGS. 2-5 will be discussed together.

The smart cap 18 can include a cap 20, a spring 22, a conductive plate 24, a spacer 26, a battery holder 28, a battery 30, a measuring device 32, and a light source 34, among other components not specifically listed. The cap 20 is axially aligned with the plunge rod 14, and the cap 20 encompasses each of the spring 22, the conductive plate 24, the spacer 26, the battery holder 28, the battery 30, the measuring device 32, and the light source 34. The cap 20 is configured to cover and protect each of the components within the smart cap 18 from damage from environmental debris as well as from other sources. The closed end 36 of the cap 20 is positioned furthest from the plunge end 16 of the plunge rod 14. The closed end 36 is the end or surface of the cap 20 that a user presses to cause the plunge rod 14 to translate axially along the axis AA of the plunge rod 14 to dispense or expel the fluid from within the barrel 12 of the syringe 10. In some examples, the cap 20 can be constructed from a polymeric, metallic, or other known material.

As shown best in FIGS. 3 and 5, the spring 22 can be a generally flat circular component with spring extensions 38 extending from the outer circumference of the circular shaped spring 22. The spring extensions 38 extend generally perpendicular to the circular portion of the spring 22, in a direction generally parallel to a central axis of the spring 22. In the illustrated example, the spring 22 includes two spring extensions 38 extending from the spring 22. In other examples, the spring 22 can include more or less than two spring extensions 38 extending from the spring 22. The spring extensions 38 are configured to extend to a lower surface 32B of the measuring device 32, which is positioned closer to the plunge end 16 than the spring 22. Specifically, the spring extensions 38 are configured to be coupled to the lower surface 32B of the measuring device 32 (based on the orientation illustrated in FIGS. 2-3). More specifically, a tab 40 positioned at an end of each of the spring extensions 38 is configured to engage and abut the lower surface 32B of the measuring device 32, coupling the spring 22 to the measuring device 32. The spacer 26 is configured to ensure a gap remains present between the spring 22 and the battery holder 28, discussed further below.

The conductive plate 24 is coupled to the spring 22 such that the conductive plate 24 cannot translate or otherwise move relative to the spring 22. More specifically, the conductive plate 24 is coupled to a lower surface 22B of the spring 22 that faces the plunge end 16 of the plunge rod 14, which lower surface 22B also faces the battery holder 28. The conductive plate 24 is axially offset from the battery holder 28, such that a gap is formed between an axial underside (i.e., a lower surface 24B) of the conductive plate 24 and an axial topside (i.e., an upper surface 28A) of the battery holder 28, with reference to axis AA. More specifically, the spacer 26 is positioned between the conductive plate 24 and the battery holder 28, creating the gap between the conductive plate 24 and the spacer 26. In some examples, the spacer 26 is a washer, such as a plastic washer. In other examples, the spacer 26 can be a washer constructed from a material other than plastic. Further, as illustrated in FIG. 5, in some examples the spacer 26 can have the shape of a generally flat ring. In other examples, the spacer 26 can have a shape other than a generally flat ring. The spacer 26 acts as a fixed thickness washer to control a distance between the conductive plate 24 and the battery holder 28 and/or battery 30 during assembly of the smart cap 18, and at rest when no force is applied to the smart cap 18.

The conductive plate 24 is an electrically conductive component that is constructed from an electrically conductive material, such as, for example, copper or aluminum. As such, in some examples, the conductive plate 24 can be coupled to the spring 22 through various fastening means, such as welding, soldering, brazing, or various adhesives, among other options not specifically listed. In other examples, the conductive plate 24 can be coupled to the spring 22 through mechanical means, such as a fastener, snap-fit connections, or interference fit, among other options not specifically listed. In some examples, the conductive plate 24 can have the shape of a generally flat circular disk. In other examples, the conductive plate 24 can have a shape other than a generally flat circular disk. The conductive plate 24 can be utilized as a first electrode for a variable capacitor force sensor, discussed further below.

As shown best in FIG. 5, the battery holder 28 can have generally the same shape as the spring 22. Specifically, the battery holder 28 can be a generally flat circular component with battery holder extensions 42 extending from the outer circumference of the circular shaped battery holder 28. The battery holder extensions 42 extend generally perpendicular to the circular portion of the battery holder 28, in a direction generally parallel to a central axis of the battery holder 28. In the illustrated example, the battery holder 28 includes two battery holder extensions 42 extending from the battery holder 28. In other examples, the battery holder 28 can include more or less than two battery holder extensions 42 extending from the battery holder 28. The battery holder extensions 42 are configured to extend to the lower surface 32B of the measuring device 32, which is positioned closer to the plunge end 16 than the battery holder 28. Specifically, the battery holder extensions 42 are configured to be coupled to the lower surface 32B of the measuring device 32 (based on the orientation illustrated in FIGS. 2-3). More specifically, a tab 44 positioned at an end of each of the battery holder extensions 42 is configured to engage and abut the lower surface 32B of the measuring device 32, coupling the battery holder 28 to the measuring device 32.

The battery holder 28 is positioned axially closer to the plunge end 16 than the spacer 26, the conductive plate 24, and the spring 22. Further, a lower surface 28B of the battery holder 28 is positioned adjacent and contacts an upper surface 30A of the battery 30. More specifically, an axial underside (lower surface 28B) of the battery holder 28 abuts an axial topside (upper surface 30A) of the battery 30. The battery holder 28 is configured to hold and secure the battery 30 within the cap 20 of the smart cap 18. Further, battery holder 28 is configured to secure the battery 30 to the measuring device 32. The battery holder 28 can be constructed from an electrically conductive material, such as, for example, copper or aluminum. As such, the battery holder 28 and/or the battery 30 can be utilized as a second electrode for a variable capacitor force sensor, discussed further below.

As discussed, the battery 30 can be positioned axially between the battery holder 28 and the measuring device 32. Therefore, an upper surface 32A of the measuring device 32 can be positioned adjacent and abut a lower surface 30B of the battery 30. As illustrated, in some examples, the battery 30 can be a button cell or coin cell battery 30. Therefore, the battery 30 can be a small, circular disc that is configured to store electrical energy. Further, the battery 30 can be configured to supply electrical energy to the smart cap 18 for the smart cap 18 to operate and function. More specifically, the battery 30 can be configured to supply electrical energy to the measuring device 32 and the light source 34, and the battery 30 can be utilized to supply the electrical current utilized to measure the conductance between the first electrode and the second electrode, discussed further below. In some examples, as illustrated, the battery 30 is axially aligned with the axis AA of the plunge rod 14.

The measuring device 32 is disposed axially closer to the plunge end 16 than the battery 30, the battery holder 28, the spacer 26, the conductive plate 24, and the spring 22. In addition, the measuring device 32 is axially aligned with each of the battery 30, the battery holder 28, the spacer 26, the conductive plate 24, and the spring 22, and the measuring device 32 is also axially aligned with the axis AA of the plunge rod 14. In some examples, as illustrated best in FIG. 5, the measuring device 32 can have a generally flat circular shape. In other examples, the measuring device 32 can have a shape other than a generally flat circular shape. The measuring device 32 can be configured to measure and record capacitance measurements, discussed further below.

In some examples, the measuring device 32 can be a printed circuit board that is configured to record capacitance measurements and store the capacitance measurements within a memory 46 of the printed circuit board (measuring device 32). As such, in some examples, the smart cap 18 can be configured as a variable capacitor force sensor. The variable capacitor force sensor can be constructed from a first electrode and a second electrode. In some examples, the first electrode can be the conductive plate 24 coupled to the spring 22, and the second electrode can be one of the battery 30 or the battery holder 28. In other examples, the first electrode can be the conductive plate 24 coupled to the spring 22, and the second electrode can be a conductive copper pad coupled to the upper or topside of the measuring device 32. In either example, the measuring device 32 is configured to measure the capacitance between the first electrode and the second electrode, which can be processed and output as an input force measurement (i.e., force value). Further, in some examples, the capacitance measurements measured by the measuring device 32 can be downloaded to a separate processing device (e.g. a computer) for further processing and analysis.

When a force is applied to the smart cap 18, such as when a user presses and squeezes the closed end 36 of the cap 20 of the smart cap 18 towards the barrel 12, it causes the plunge rod 14 to translate axially into the barrel 12. Further, the pressing or squeezing force on the smart cap 18 causes the first electrode (conductive plate 24) to translate axially towards the second electrode (battery holder 28, battery 30, or copper pad of the measuring device 32) within the cap 20. The measuring device 32 is configured to continuously take capacitance measurements between the first and second electrodes and store the capacitance measurements within the memory 46 of the measuring device 32. Then the measuring device 32 is configured to calculate a change in capacitance measured between the first and second electrodes during the depression of the smart cap 18 and the plunge rod 14 (i.e., during the injection process). The change in capacitance can be computed and converted to identify a change in distance between the first and second electrodes, which can then be computed and converted to identify the compression experienced by the spring 22 (based on the known compression characteristics of the spring 22). Lastly, the compression of the spring 22 can be computed and converted to identify and output the force value applied to the smart cap 18 and the plunge rod 14 during the injection process.

Specifically, a higher compression force leads to a smaller gap between the first and second electrodes, which can be computed and output as a force value by the measuring device 32. A lower compression force leads to a larger gap between the first and second electrodes, which can be computed and output as a force value by the measuring device 32.

It is to be understood that the spring 22 is electrically conductively coupled to the conductive plate 24, and the spring 22 is electrically conductively coupled to the measuring device 32 through the tabs 40 of the spring extensions 38 of the spring 22. Therefore, the spring 22 acts as an electrical conductor and the spring 22 is configured to electrically connect the conductive plate 24 to the measuring device 32 for signal transfer therebetween. In addition, it is to be understood that the battery 30 and the battery holder 28 are each electrically conductively coupled to the measuring device 32 through the tabs 44 of the battery holder extensions 42 of the battery holder 28. Therefore, the battery holder 28 acts as an electrical conductor and the battery holder 28 is configured to electrically connect the battery 30 to the measuring device 32 for signal transfer therebetween.

Lastly, it is to be understood that each of the converting and computing steps described in the previous paragraphs are performed by the measuring device 32 (i.e., the printed circuit board). As such, the measuring device 32 is configured to receive the capacitance measurements, perform converting and computing steps/processes, and then output a force value indicating the force that was applied to the smart cap 18 and the plunge rod 14 during the injection process. The aforementioned information can be utilized to provide more refined insights and perform better statistical analysis of medical trial outcomes. Further, the aforementioned information can be utilized to verify that an air priming has been performed before proceeding with the injection, ensuring safety among other advantages not specifically discussed.

Referring now to FIG. 4, which is a perspective view of the smart cap 18 with the light source 34 glowing or illuminating through the cap 20 of the smart cap 18. The light source 34 can be configured to illuminate once a compression force applied to the smart cap 18 exceeds a predefined limit. As such, the light source 34 can indicate to a user if and when they are applying a force to the smart cap 18 and plunge rod 14 that is greater than the optimal compression force, preventing the user from injecting the fluid within the syringe 10 at a faster than desirable rate. The predefined limit value can vary depending on the fluid or liquid that is within the syringe 10 and being injected into the user. Further, the predefined limit can be any one of a mathematically calculated value, an experimental value, or a theoretical value based on previous data. In some examples, the light source 34 can be a light-emitting diode (LED) that glows or illuminates when electricity is provided to the LED. In other examples, the light source 34 can be a different light source other than an LED that glows or illuminates when electricity is provided to the light source 34. Further, in some examples, the smart cap 18 may not include the light source 34.

The smart cap 18 of the present disclosure provides many advantages that will be appreciated by persons having ordinary skill in the art, compared to previous smart syringe solutions and technologies. Specifically, the smart cap 18 according to the present disclosure improves the cost of the sensing subsystem, making the measurement more affordable and easier to integrate. In turn this creates a new generation of smart syringes that are able to monitor the injection profile over time and complement the data set recorded in real time in clinical trials. Further, the capacitive measurements taken by the smart cap 18 requires less electrical current and energy compared to force sensing resistors (FSR), achieving a longer battery life for the smart cap 18. Additionally, the conductive plate 24 being mechanically connected to the spring 22 allows for an efficient use of the conductive area and improves the linearity and signal to noise ratio of the measuring device 32 and the overall smart cap 18. Also, the use of the battery holder 28 as an electrode reduces the overall part count of the smart cap 18, reducing the cost of material and assembly time for the smart cap 18. The smart cap 18 is a scalable concept that can be applied to other products in the medical industry, as well as other products outside the medical industry, providing a low cost wireless sensing node for force and/or weight measurements.

Overall, the smart cap 18 of the syringe 10 provides a cost reduction for disposable as well as non-disposable smart syringe modules, which is achieved by the disclosed new force sensing solution. In other words, the typical force sensing resistor (FSR) has been replaced with a variable capacitor which relies on cheaper sheet metal parts and leverages the battery holder as a counter electrode, resulting in a smaller, more efficient, and cheaper sensing module/solution. Lastly, the smart cap 18 is smaller, simpler, and easier to assemble (compared to previous smart syringes) due to the miniaturized structure, fewer part count, and ease of assembly, resulting in an overall cost reduction for smart syringe solutions. The aforementioned advantages are only some of the advantages provided by the smart cap 18 and syringe 10 of the present disclosure, as will be appreciated by persons having ordinary skill in the art.

Having thus described the present embodiments in detail, it is to be appreciated and will be apparent to those skilled in the art that many physical changes, only a few of which are exemplified in the detailed description of the disclosure, could be made without altering the inventive concepts and principles embodied therein.

It is also to be appreciated that numerous embodiments incorporating only part of the preferred embodiment are possible which do not alter, with respect to those parts, the inventive concepts and principles embodied therein. The present embodiment and optional configurations are therefore to be considered in all respects as exemplary and/or illustrative and not restrictive, the scope of the disclosure being indicated by the appended claims rather than by the foregoing description, and all alternate embodiments and changes to this embodiment which come within the meaning and range of equivalency of said claims are therefore to be embraced therein.

What is claimed is:

1. A syringe comprising:

a barrel and a plunge rod axially translatable within the barrel along an axis of the plunge rod, the plunge rod including a plunge end extending outside the barrel;

a smart cap is coupled to the plunge end of the plunge rod extending outside the barrel, the smart cap comprising:

a spring including a conductive plate coupled to the spring;

a spacer disposed axially closer to the plunge end than the spring and the conductive plate;

a battery holder disposed axially closer to the plunge end than the spacer, the battery holder being adjacent a first surface of a battery;

a measuring device disposed axially closer to the plunge end than the battery holder, the measuring device being adjacent a second surface of the battery; and a cap axially aligned with the plunge rod, the cap encompassing each of the spring, the conductive plate, the spacer, the battery holder, the battery, and the measuring device.

2. The syringe of claim 1, wherein a spring extension of the spring is coupled to a surface of the measuring device facing the plunge end.

3. The syringe of claim 1, wherein the conductive plate is coupled to a surface of the spring facing the battery holder.

4. The syringe of claim 1, wherein the conductive plate is axially offset from the battery holder, with the spacer being positioned between an axial underside of the conductive plate and an axial topside of the battery holder.

5. The syringe of claim 1, wherein an axial underside of the battery holder abuts an axial topside of the battery, and an axial topside of the measuring device abuts an axial underside of the battery.

6. The syringe of claim 1, wherein a battery holder extension of the battery holder is coupled to a surface of the measuring device facing the plunge end.

7. The syringe of claim 1, wherein the measuring device is a printed circuit board.

8. The syringe of claim 7, wherein the printed circuit board is configured to record capacitance measurements and store the capacitance measurements within a memory of the printed circuit board.

9. The syringe of claim 1, wherein the smart cap is configured as a variable capacitor force sensor.

10. The syringe of claim 9, wherein the variable capacitor force sensor is constructed from a first electrode and a second electrode, the first electrode being the conductive plate coupled to the spring and the second electrode being one of the battery or the battery holder.

11. The syringe of claim 10, wherein a force applied to the smart cap causes the plunge rod to translate axially into the barrel, the force causes the first electrode to axially translate towards the second electrode within the cap, and a change in capacitance measured by the measuring device indicates a value of the force applied to the smart cap.

12. The syringe of claim 9, wherein the variable capacitor force sensor is constructed from a first electrode and a second electrode, the first electrode being the conductive plate coupled to the spring and the second electrode being a conductive copper pad of the measuring device.

13. The syringe of claim 1, wherein the measuring device, the battery, the battery holder, the spacer, the conductive plate, and the spring are positioned axially in order from the plunge end of the plunge rod in an axial direction extending away from the plunge end and the barrel.

14. The syringe of claim 1, wherein the syringe is a pre-filled disposable syringe.

15. The syringe of claim 1, further comprising a light source configured to illuminate once a compression force applied to the smart cap exceeds a predefined limit.

16. The syringe of claim 1, wherein each of the spring, the conductive plate, the spacer, the battery holder, the battery, and the measuring device are axially aligned with the axis of the plunge rod.

* * * * *